United States Patent
Saiga

(10) Patent No.: US 10,987,087 B2
(45) Date of Patent: Apr. 27, 2021

(54) ULTRASOUND ENDOSCOPE

(71) Applicant: OLYMPUS CORPORATION, Tokyo (JP)

(72) Inventor: Kazuya Saiga, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 310 days.

(21) Appl. No.: 16/226,850

(22) Filed: Dec. 20, 2018

(65) Prior Publication Data
US 2019/0117192 A1 Apr. 25, 2019

Related U.S. Application Data

(63) Continuation of application No. PCT/JP2017/008507, filed on Mar. 3, 2017.

(30) Foreign Application Priority Data

Jun. 29, 2016 (JP) .............................. JP2016-129287

(51) Int. Cl.
*A61B 8/00* (2006.01)
*A61B 8/12* (2006.01)
(Continued)

(52) U.S. Cl.
CPC .......... *A61B 8/4461* (2013.01); *A61B 1/0008* (2013.01); *A61B 1/00091* (2013.01);
(Continued)

(58) Field of Classification Search
CPC . A61B 8/4461; A61B 1/0008; A61B 1/00091; A61B 1/00094; A61B 8/445; A61B 8/12; A61B 1/0661; A61B 8/4488
See application file for complete search history.

(56) References Cited

U.S. PATENT DOCUMENTS 4,779,624 A 10/1988 Yokoi
5,471,988 A * 12/1995 Fujio ........................ A61B 8/12
600/439
(Continued)

FOREIGN PATENT DOCUMENTS

CN 101394792 A 3/2009
JP H09-135834 A 5/1997
(Continued)

OTHER PUBLICATIONS

International Search Report dated May 23, 2017 issued in PCT/JP2017/008507.
(Continued)

*Primary Examiner* — Joel Lamprecht
(74) *Attorney, Agent, or Firm* — Scully, Scott, Murphy & Presser, P.C.

(57) ABSTRACT

An ultrasound endoscope is provided with an insertion portion to be inserted into a subject along a first direction which is an insertion direction. The ultrasound endoscope includes: a transducer having a scanning surface that scans with an ultrasound wave along a second direction; a supply pipeline configured to supply an ultrasound wave transfer medium; and a rigid member connected to a proximal end side of the transducer, the rigid member formed with a scanning surface supply port configured to supply the ultrasound wave transfer medium supplied from the supply pipeline in a direction intersecting with the first direction and the second direction.

7 Claims, 8 Drawing Sheets

(51) Int. Cl.
*A61B 1/00* (2006.01)
*A61B 1/06* (2006.01)

(52) U.S. Cl.
CPC .......... *A61B 1/00094* (2013.01); *A61B 8/12* (2013.01); *A61B 8/445* (2013.01); *A61B 1/0661* (2013.01); *A61B 8/4488* (2013.01)

(56) References Cited

U.S. PATENT DOCUMENTS

2006/0241472 A1  10/2006  Osawa et al.
2009/0005689 A1   1/2009  Kodama et al.
2017/0014099 A1*  1/2017  Morimoto .............. A61B 8/445

FOREIGN PATENT DOCUMENTS

| JP | 2005-261857 A | 9/2005 |
| JP | 2006-239240 A | 9/2006 |

OTHER PUBLICATIONS

Chinese Office Action dated Feb. 8, 2021 received in 201780040286.8.

\* cited by examiner

ULTRASOUND ENDOSCOPE

CROSS-REFERENCE TO RELATED APPLICATION

This application is a continuation of PCT International Application No. PCT/JP2017/008507 filed on Mar. 3, 2017 which claims the benefit of priority from Japanese Patent Application No. 2016-129287, filed on Jun. 29, 2016, the entire contents of which are incorporated herein by reference.

BACKGROUND

1. Technical Field

The present disclosure relates to an ultrasound endoscope.

2. Related Art

In the related art, known are ultrasound endoscopes that perform observation of the inside of a subject by inserting a flexible and thin long insertion portion into a subject such as a person and transmitting and receiving ultrasound waves by an ultrasound transducer provided on the distal end side of the insertion portion (for example, see JP H9-135834 A).

Meanwhile, ultrasound waves have a very low propagation rate in the air. Therefore, in ultrasound diagnosis by an ultrasound endoscope, in order to suppress a decrease in the propagation rate of ultrasound waves, a degassed water-filling method or a balloon method described below are adopted.

In the degassed water-filling method, degassed water having been subjected to gas removal treatment is supplied to the inside of a subject (for example, the stomach) from the distal end of the insertion portion. Ultrasound diagnosis is performed in a state in which degassed water is interposed between the ultrasound transducer and a body wall inside the subject.

In the balloon method, a balloon which is freely inflatable and deflatable is disposed at the distal end of the insertion portion to cover the ultrasound transducer. Then, ultrasound diagnosis is performed in a state in which the balloon is filled with degassed water and thereby inflated.

SUMMARY

In some embodiments, an ultrasound endoscope is provided with an insertion portion to be inserted into a subject along a first direction which is an insertion direction. The ultrasound endoscope includes: a transducer having a scanning surface that scans with an ultrasound wave along a second direction; a supply pipeline configured to supply an ultrasound wave transfer medium; and a rigid member connected to a proximal end side of the transducer, the rigid member formed with a scanning surface supply port configured to supply the ultrasound wave transfer medium supplied from the supply pipeline in a direction intersecting with the first direction and the second direction.

The above and other features, advantages and technical and industrial significance of this disclosure will be better understood by reading the following detailed description of presently preferred embodiments of the disclosure, when considered in connection with the accompanying drawings.

DETAILED DESCRIPTION

An embodiment for carrying out the disclosure (hereinafter referred to as the "embodiment") will be described below with reference to the drawings. Note that the disclosure is not limited by the embodiment described below. In description of the drawings, the same part is denoted by the same symbol.

Schematic Configuration of Endoscope System

Figure 1:
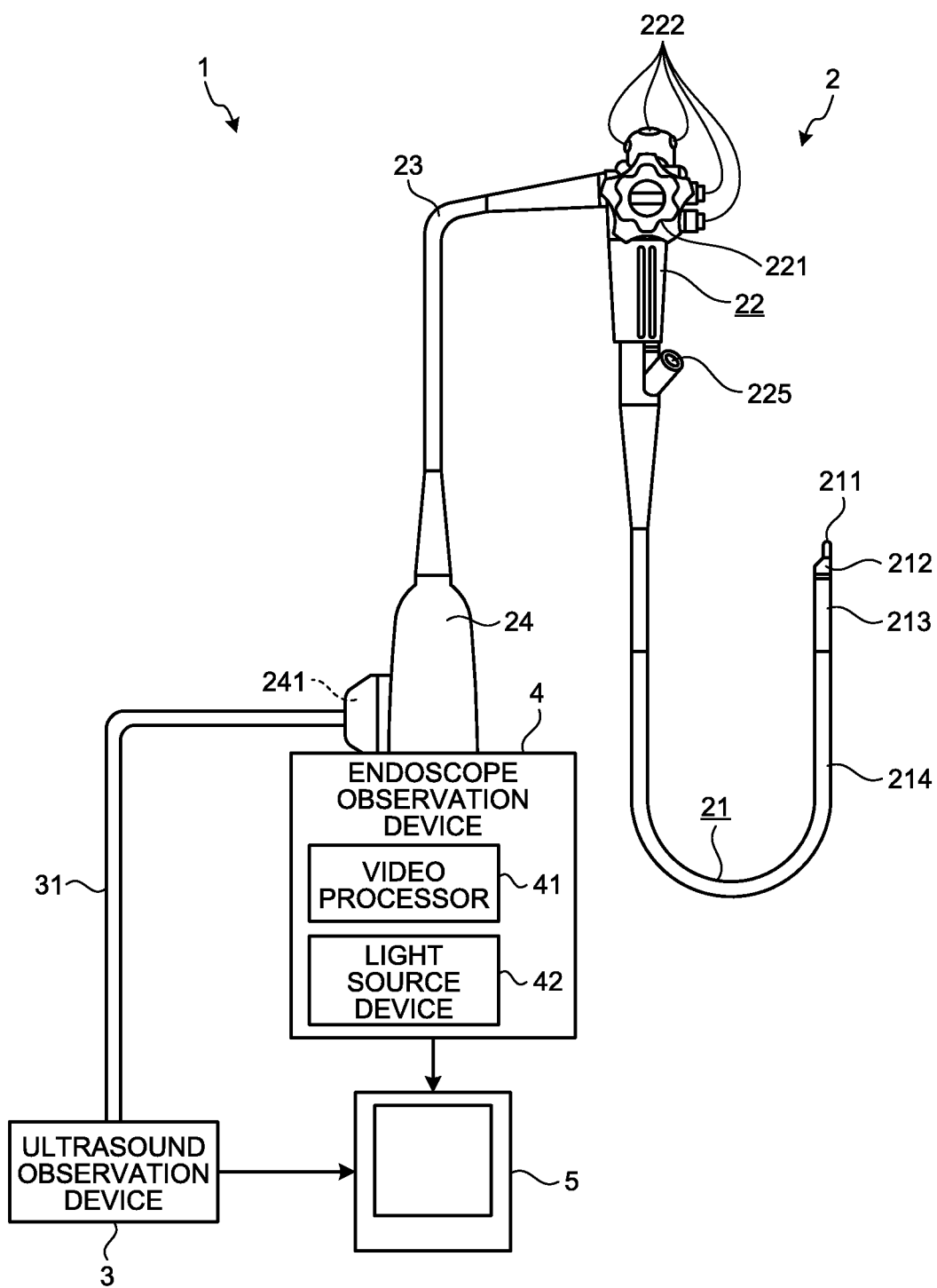
FIG. 1 is a diagram schematically illustrating an endoscope system according to an embodiment of the disclosure.

FIG. 1 is a diagram schematically illustrating an endoscope system 1 according to an embodiment of the disclosure.

The endoscope system 1 is performs ultrasound diagnosis on the inside of a subject such as a person by using an ultrasound endoscope. As illustrated in FIG. 1, the endoscope system 1 includes an ultrasound endoscope 2, an ultrasound observation device 3, an endoscope observation device 4, and a display device 5.

A part of the ultrasound endoscope 2 can be inserted into the subject and has a function of transmitting an ultrasound pulse toward a body wall inside the subject, receiving an ultrasound echo reflected by the subject and outputting an echo signal as well as a function of imaging the inside of the subject and outputting an image signal.

Note that a detailed structure of the ultrasound endoscope 2 will be described later.

The ultrasound observation device 3 is electrically connected to the ultrasound endoscope 2 via an ultrasound cable 31 (FIG. 1) and outputs a pulse signal to the ultrasound endoscope 2 via the ultrasound cable 31 and receives an echo signal from the ultrasound endoscope 2. The ultrasound observation device 3 performs predetermined processing on the echo signal to generate an ultrasound image.

The endoscope observation device 4 is detachably connected with an endoscope connector 24 (FIG. 1) of the ultrasound endoscope 2 which will be described later. As illustrated in FIG. 1, the endoscope observation device 4 includes a video processor 41 and a light source device 42.

The video processor 41 receives an image signal from the ultrasound endoscope 2 via the endoscope connector 24. The video processor 41 then performs predetermined processing on the image signal to generate an endoscopic image.

The light source device 42 supplies illumination light for illuminating the inside of the subject to the ultrasound endoscope 2 via the endoscope connector 24.

The display device 5 includes liquid crystal or organic electro luminescence (EL) and displays the ultrasound image generated by the ultrasound observation device 3, the endoscopic image generated by the endoscope observation device 4, etc.

Structure of Ultrasound Endoscope

As illustrated in FIG. 1, the ultrasound endoscope 2 includes an insertion portion 21, an operating unit 22, a universal cable 23, and the endoscope connector 24.

Note that a "distal end side" referred to hereinbelow means the distal end side of the insertion portion 21 (the distal end side in the direction of insertion into a subject). Moreover, a "proximal end side" referred to hereinbelow means a side extends away from the distal end of the insertion portion 21.

The insertion portion 21 is a portion to be inserted into a subject. As illustrated in FIG. 1, the insertion portion 21 includes an ultrasound probe 211 included on the distal end side, a rigid member 212 connected to the proximal end side of the ultrasound probe 211, a bending unit 213 which is bendable and is connected to the proximal end side of the rigid member 212, and a flexible tube 214 which is flexible and is connected to the proximal end side of the bending unit 213.

Here, inside the insertion portion 21, the operating unit 22, the universal cable 23, and the endoscope connector 24, a light guide (not illustrated) for transmitting the illumination light supplied from the light source device 42 and a plurality of signal cables (not illustrated) for transmitting the above-described pulse signal, echo signal, and image signal are routed.

Note that a detailed structure (the ultrasound probe 211 and the rigid member 212) of the distal end side of the insertion portion 21 will be described later.

The operating unit 22 is connected to the proximal end side of the insertion portion 21 and accepts various types operation from a doctor or the like. As illustrated in FIG. 1, the operating unit 22 includes a bending knob 221 for bending operation of the bending unit 213 and a plurality of operating members 222 for performing various types of operation.

Figure 4:
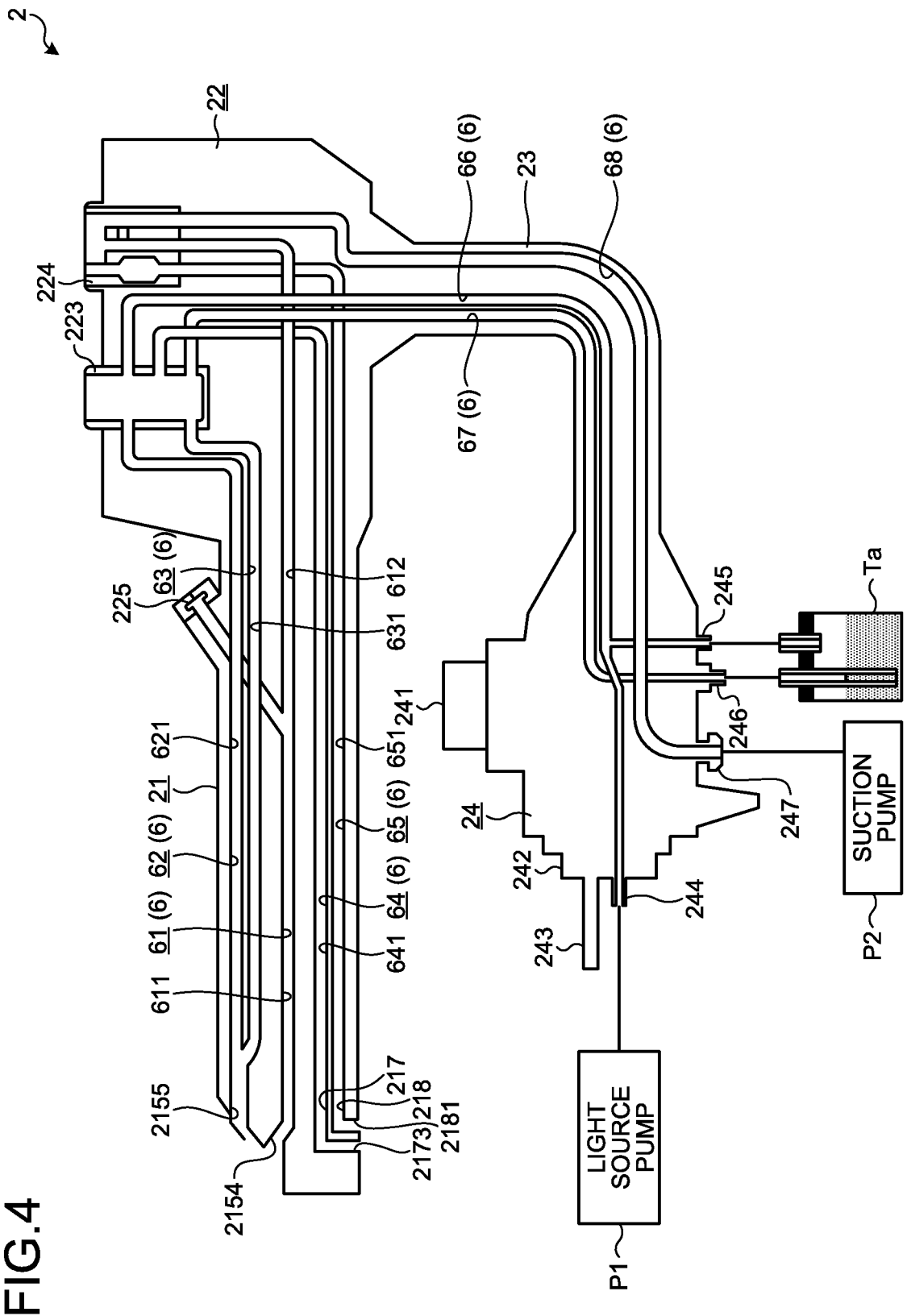
FIG. 4 is a diagram for explaining a plurality of pipelines included in an ultrasound endoscope.

Here, the insertion portion 21 and the operating unit 22 include first to fifth distal-end-side pipelines 61 to 65 (see FIG. 4). The operating unit 22 further includes first and second cylinders 223 and 224 (see FIG. 4) communicating with the first to fifth distal-end-side pipelines 61 to 65. Furthermore, the first and second cylinders 223 and 224 are attached with first and second pipeline switching valves 2231 and 2241 (see FIGS. 5 to 8), respectively, which form a part of the plurality of operating members 222 and switch connection statuses between the first to fifth distal-end-side pipelines 61 to 65 and first to third proximal-end-side pipelines 66 to 68 (see FIG. 4), which will be described later, in response to operation by a doctor or the like.

Note that the first to fifth distal-end-side pipelines 61 to 65 and the first to third proximal-end-side pipelines 66 to 68 correspond to the plurality of pipelines 6 according to the disclosure. A detailed structure of the plurality of pipelines 6 will be described later. The connection statuses of the plurality of pipelines 6 depending on operation of the first and second pipeline switching valves 2231 and 2241 will also be described later.

The universal cable 23 extends from the operating unit 22 and includes the above-described light guide (not illustrated) or a plurality of signal cables (not illustrated) routed therein.

The endoscope connector 24 is provided at an end of the universal cable 23. The endoscope connector 24 includes an endoscope connector 241 (FIG. 1) to be connected with the ultrasound cable 31 and a plug unit 242 (see FIG. 4) inserted in the endoscope observation device 4 and connected to the video processor 41 and the light source device 42.

Here, the operating unit 22, the universal cable 23, and the endoscope connector 24 includes the first to third proximal-end-side pipelines 66 to 68 (see FIG. 4) communicating with the first and second cylinders 223 and 224 included in the operating unit 22.

Moreover, the plug unit 242 includes a plurality of electrical contacts (not illustrated), a light guide base 243 (see FIG. 4), and an air supply base 244 (see FIG. 4).

The plurality of electrical contacts are portions electrically connected to the video processor 41 when the endoscope connector 24 is inserted into the endoscope observation device 4.

The light guide base 243 is a portion that optically connects the light guide and the light source device 42 when an incident end side of the above-described light guide (not illustrated) is inserted and the endoscope connector 24 is inserted into the endoscope observation device 4

The air supply base 244 is a portion connected to a light source pump P1 (see FIG. 4) included inside the light source device 42 when the endoscope connector 24 is inserted into the endoscope observation device 4.

The endoscope connector 24 further includes first and second water supply bases 245 and 246 (see FIG. 4) to which an external water supply tank Ta (see FIG. 4) is connected separately and a suction base 247 (see FIG. 4) to which an external suction pump P2 (see FIG. 4) is connected.

Structure of Insertion Portion

Figure 2:
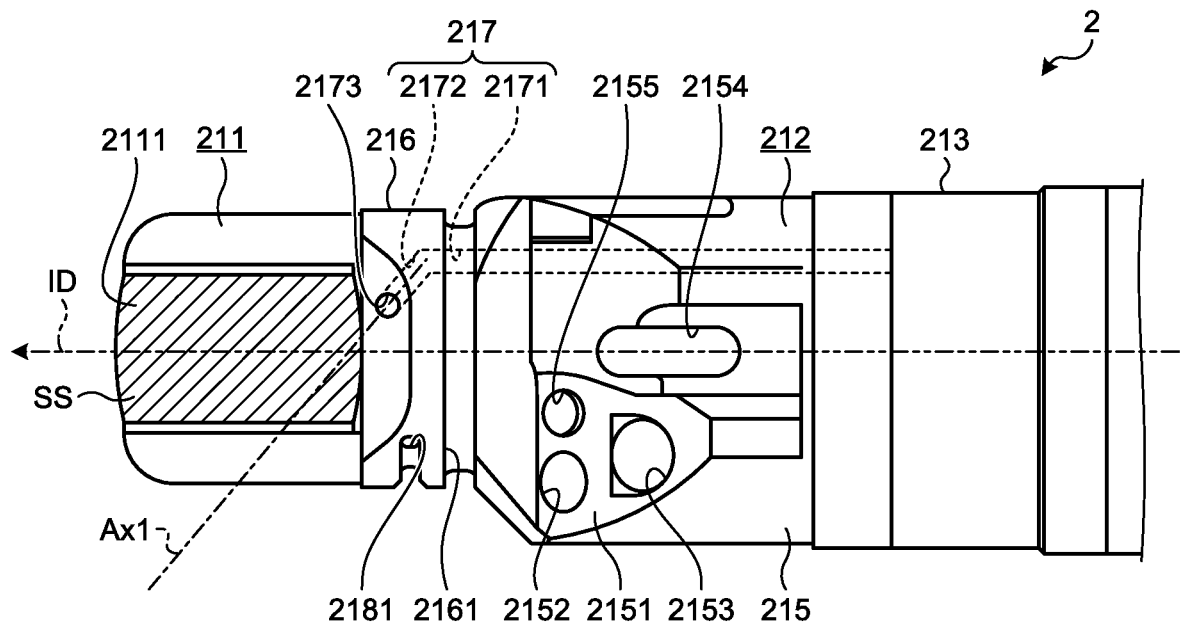
FIG. 2 is an enlarged view of a distal end side of an insertion portion.
Figure 3:
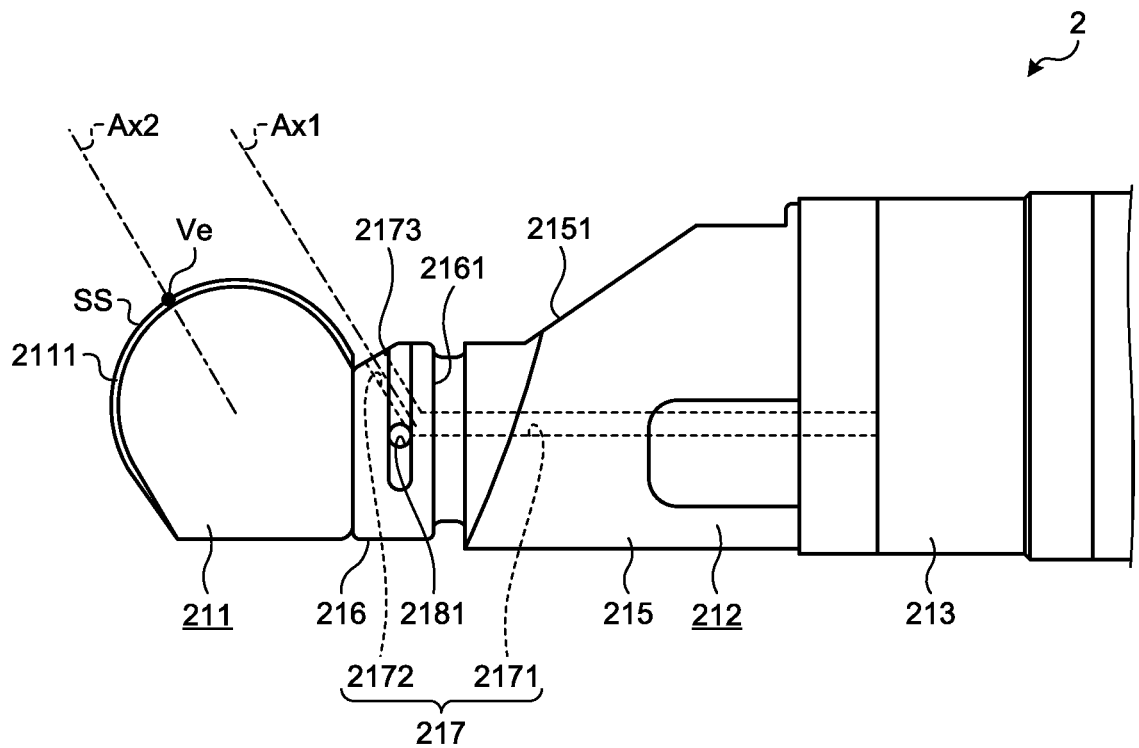
FIG. 3 is an enlarged view of the distal end side of the insertion portion.

FIGS. 2 and 3 are enlarged views of the distal end side of the insertion portion 21. Specifically, FIG. 2 is a view of the distal end side of the insertion portion 21 as viewed from the upper side of the insertion portion 21 (a direction orthogonal to the insertion direction ID of the insertion portion 21 and to a scanning surface SS of a transducer 2111). FIG. 3 is a view of the distal end side of the insertion portion 21 as viewed from the side (a direction orthogonal to the insertion direction ID and extends along the scanning surface SS).

Note that, in FIG. 2, the scanning surface SS is hatched for convenience of explanation.

Hereinafter, structures of the ultrasound probe 211 and the rigid member 212 will be described in an order with reference to FIGS. 2 and 3.

Structure of Ultrasound Probe

As illustrated in FIG. 2 or FIG. 3, the ultrasound probe 211 has a transducer 2111 in which a plurality of ultrasound transducers is regularly arrayed.

Here, an ultrasound transducer has an acoustic lens, a piezoelectric element, and a matching layer, and acquires an ultrasound echo contributing to an ultrasound tomographic image of an inner part than the body wall inside the subject.

The transducer 2111 converts the pulse signal input from the ultrasound observation device 3 via the above-described signal cable (not illustrated) into an ultrasound pulse and transmits the ultrasound pulse to the inside of the subject. The transducer 2111 further converts the ultrasound echo reflected inside the subject into an electrical echo signal and outputs the echo signal to the ultrasound observation device 3 via the above-described signal cable (not illustrated).

In the present embodiment, the transducer 2111 is a convex type and has the scanning surface SS having an arc shape in the cross-sectional view thereof with the plurality of ultrasound transducers regularly arranged so as to form the convex arc. That is, the transducer 2111 is capable of scanning with an ultrasound wave in a fan shape spreading in a normal direction of the scanning surface SS.

Structure of Rigid Member

The rigid member 212 is made of a resin material. As illustrated in FIG. 2 or FIG. 3, the rigid member 212 includes a large diameter portion 215 and a small diameter portion 216.

The large diameter portion 215 is a portion to which the bending unit 213 is connected and has a substantially cylindrical shape extending along the insertion direction ID of the insertion portion 21. In the large diameter portion 215, on the upper side, a tapered surface 2151 that gradually reduces the diameter of the large diameter portion 215 toward the distal end side is formed.

Moreover, as illustrated in FIG. 2, in the large diameter portion 215, an illumination hole 2152, an imaging hole 2153, a treatment instrument channel 2154, and an air/water supply hole 2155 each penetrating from the proximal end of the large diameter portion 215 to the tapered surface 2151 are formed.

Inside the illumination hole 2152, an emission end side of the above-described light guide (not illustrated) is inserted. The illumination light supplied from the light source device 42 is emitted to the inside of the subject via the illumination hole 2152.

Inside the imaging hole 2153, an objective optical system (not illustrated) that collects light emitted from the light source device 42 and reflected inside the subject (subject image) and an image sensor (not illustrated) for imaging the subject image, light of which is collected by the objective optical system, are disposed. The image signal captured by the image sensor is transferred to the endoscope observation device 4 (video processor 41) via the above-described signal cable (not illustrated).

The treatment instrument channel 2154 forms a part of the first distal-end-side pipeline 61.

The air/water supply hole 2155 forms a part of the second and third distal-end-side pipelines 62 and 63.

The small diameter portion 216 has a substantially cylindrical shape (substantially cylindrical shape having an outer diameter dimension smaller than that of the large diameter portion 215) extending along the insertion direction of the insertion portion 21 and is formed integrally with and at the distal end of the large diameter portion 215.

A balloon attachment groove 2161 for attachment of a balloon (not illustrated), which is freely inflatable and deflatable and the inside of which is to be filled with water, is formed on the outer periphery on the proximal end side of the small diameter portion 216.

When the balloon is attached, the ultrasound probe 211 is inserted into the balloon from the mouth portion of the balloon (mouth portion for allowing degassed water to flow into the balloon). Then, the mouth portion of the balloon is hooked on the balloon attachment groove 2161. In this state, the entire ultrasound probe 211 is covered with the balloon.

Meanwhile, as indicated by a broken line in FIG. 2 or 3, in the large diameter portion 215 and the small diameter portion 216, a water supply hole 217 penetrating from the proximal end of the large diameter portion 215 to the upper side of the outer peripheral surface of the small diameter portion 216 is formed.

The water supply hole 217 includes: a first water supply hole 2171 extending from the proximal end of the large diameter portion 215 to the small diameter portion 216 along the insertion direction ID of the insertion portion 21; and a second water supply hole 2172, communicating with the first water supply hole 2171, extending while bended with respect to the first water supply hole 2171, and penetrating through to the upper side of the outer peripheral surface of the small diameter portion 216.

Hereinafter, a through hole penetrating through to the upper side of the outer peripheral surface of the small diameter portion 216 in the second water supply hole 2172 is referred to as a scanning surface supply port 2173.

More specifically, as illustrated in FIG. 2, when the distal end of the insertion portion 21 is viewed from the upper side thereof, the water supply hole 217 is formed such that a part of a supply central axis Ax1 that passes through the scanning surface supply port 2173 and is obtained by extending the central axis of the second water supply hole 2172 is positioned within the scanning surface SS. Moreover, as illustrated in FIG. 2, when the distal end of the insertion portion 21 is viewed from the upper side thereof, the water supply hole 217 is formed such that the scanning surface supply port 2173 is at a position shifted from the axis passing through the center in the width direction of the scanning surface SS and that the supply central axis Ax1 intersects with the insertion direction ID of the insertion portion 21 at an acute angle. Moreover, as illustrated in FIG. 3, when the distal end of the insertion portion 21 is viewed from the side, the water supply hole 217 is formed such that the supply central axis Ax1 intersects with a scanning central axis Ax1 that passes through the vertex Ve of the scanning surface SS and extending in the normal direction of the scanning surface SS at an acute angle. Furthermore, as illustrated in FIG. 2 or FIG. 3, the water supply hole 217 is formed such that the scanning surface supply port 2173 is closer to the distal end side than the balloon attachment groove 2161.

The water supply hole 217 described above forms a part of the fourth distal-end-side pipeline 64.

In addition, in the large diameter portion 215 and the small diameter portion 216, a suction hole 218 (see FIG. 4) penetrating from the proximal end of the large diameter portion 215 to a side of the outer peripheral surface of the small diameter portion 216 is formed. Note that in FIGS. 2 and 3, only a penetrating port 2181 (hereinafter, suction port 2181) penetrating through to the outer peripheral surface on the side of the small diameter portion 216 is illustrated out of the suction hole 218 for convenience of explanation.

More specifically, as illustrated in FIG. 2 or FIG. 3, the suction hole 218 is formed such that the suction port 2181 is closer to the distal end side than the balloon attachment groove 2161.

The suction hole 218 described above forms a part of the fifth distal-end-side pipeline 65.

Structure of a Plurality of Pipelines

FIG. 4 is a diagram for explaining the plurality of pipelines 6 included in the ultrasound endoscope 2.

Hereinafter, the structure of the plurality of pipelines 6 will be described with reference to FIG. 4.

As described above, the plurality of pipelines 6 includes the first to fifth distal-end-side pipelines 61 to 65 and the first to third proximal-end-side pipelines 66 to 68.

The first distal-end-side pipeline 61 is a pipeline for allowing a treatment instrument (for example, a puncture needle) to project from the distal end (treatment instrument channel 2154) of the insertion portion 21 to the outside and for sucking liquid in the subject from the distal end of the insertion portion 21. As illustrated in FIG. 4, the first distal-end-side pipeline 61 includes the treatment instrument channel 2154, a treatment instrument tube 611, and a suction tube 612.

The treatment instrument tube 611 is routed inside the bending unit 213 and the flexible tube 214 with one end communicating with the treatment instrument channel 2154. The treatment instrument tube 611 also communicates with a treatment instrument inserting port 225 (FIGS. 1 and 4) included in the operating unit 22. That is, when a treatment instrument (for example, a puncture needle) is inserted into the treatment instrument tube 611 via the treatment instrument inserting port 225, the treatment instrument protrudes to the outside from the treatment instrument channel 2154.

The suction tube 612 is routed inside the operating unit 22 with one end communicating with the other end of the treatment instrument tube 611 and the other end communicating with the second cylinder 224.

The second distal-end-side pipeline 62 is a pipeline for sending the air from the distal end (air/water supply hole 2155) of the insertion portion 21 toward the imaging hole 2153 to clean the objective optical system (not illustrated). As illustrated in FIG. 4, the second distal-end-side pipeline 62 includes the air/water supply hole 2155 and a nozzle air supply tube 621.

The nozzle air supply tube 621 is routed inside the bending unit 213, the flexible tube 214, and the operating unit 22. One end of the nozzle air supply tube 621 communicates with the air/water supply hole 2155, and the other end of the nozzle air supply tube 621 communicates with the first cylinder 223.

The third distal-end-side pipeline 63 is a pipeline for supplying water from the distal end (air/water supply hole 2155) of the insertion portion 21 toward the imaging hole 2153 to clean the objective optical system (not illustrated). As illustrated in FIG. 4, the third distal-end-side pipeline 63 includes the air/water supply hole 2155 and a nozzle water supply tube 631.

The nozzle water supply tube 631 is routed inside the bending unit 213, the flexible tube 214, and the operating unit 22. One end of the nozzle water supply tube 631 communicates with the air/water supply hole 2155, and the other end of the nozzle water supply tube 631 communicates with the first cylinder 223.

The fourth distal-end-side pipeline 64 is a pipeline for supplying an ultrasound wave transfer medium (in the present embodiment, water) from the distal end (water supply hole 217) of the insertion portion 21 toward the scanning surface SS and in the case where a balloon (not illustrated) is used, a pipeline for filling the inside of the balloon with water. As illustrated in FIG. 4, the fourth distal-end-side pipeline 64 includes a water supply hole 217 and a balloon water supply tube 641.

The balloon water supply tube 641 is routed inside the bending unit 213, the flexible tube 214, and the operating unit 22. One end of the balloon water supply tube 641 communicates with the water supply hole 217, and the other end of the balloon water supply tube 641 communicates with the first cylinder 223.

The fifth distal-end-side pipeline 65 is a pipeline for sucking water inside the balloon in the case where the balloon (not illustrated) is used. As illustrated in FIG. 4, the fifth distal-end-side pipeline 65 includes the suction hole 218 and a balloon suction tube 651.

The balloon suction tube 651 is routed inside the bending unit 213, the flexible tube 214, and the operating unit 22. One end of the balloon suction tube 651 communicates with the suction hole 218, and the other end of the balloon suction tube 651 communicates with the second cylinder 224.

The first proximal-end-side pipeline 66 is routed inside the operating unit 22, the universal cable 23, and the endoscope connector 24. One end of the first proximal-end-side pipeline 66 is branched into two, with one of them communicating with the air supply base 244 and the other communicating with a first water supply base 245, and the other end communicates with the first cylinder 223. That is, the first proximal-end-side pipeline 66 allows the air discharged from the light source pump P1 to circulate to the first cylinder 223 and the water supply tank Ta.

The second proximal-end-side pipeline 67 is routed inside the operating unit 22, the universal cable 23, and the endoscope connector 24. One end of the second proximal-end-side pipeline 67 communicates with the second water supply base 246, and the other end of the second proximal-end-side pipeline 67 communicates with the first cylinder 223. That is, the second proximal-end-side pipeline 67 allows water discharged from the water supply tank Ta to circulate to the first cylinder 223.

The third proximal-end-side pipeline 68 is routed inside the operating unit 22, the universal cable 23, and the endoscope connector 24. One end of the third proximal-end-side pipeline 68 communicates with the suction base 247, and the other end of the third proximal-end-side pipeline 68 communicates with the second cylinder 224.

Connection Status of Plurality of Pipelines Corresponding to Operation of First and Second Pipeline Switching Valves FIGS. 5 to 8 are diagrams for explaining connection statuses of the plurality of pipelines 6 depending on operation of the first and second pipeline switching valves 2231 and 2241.

As a structure of the first and second cylinders 223 and 224 and the first and second pipeline switching valves 2231 and 2241, a known structure (for example, see JP 2007-111266 A) can be adopted. For this reason, in the following, description of a detailed structure of the first and second cylinders 223 and 224 and the first and second pipeline switching valves 2231 and 2241 will be omitted. With reference to FIGS. 5 to 8, connection statuses of the plurality of pipelines 6 depending on operation of the first and second pipeline switching valves 2231 and 2241 will be described.

Figure 5:
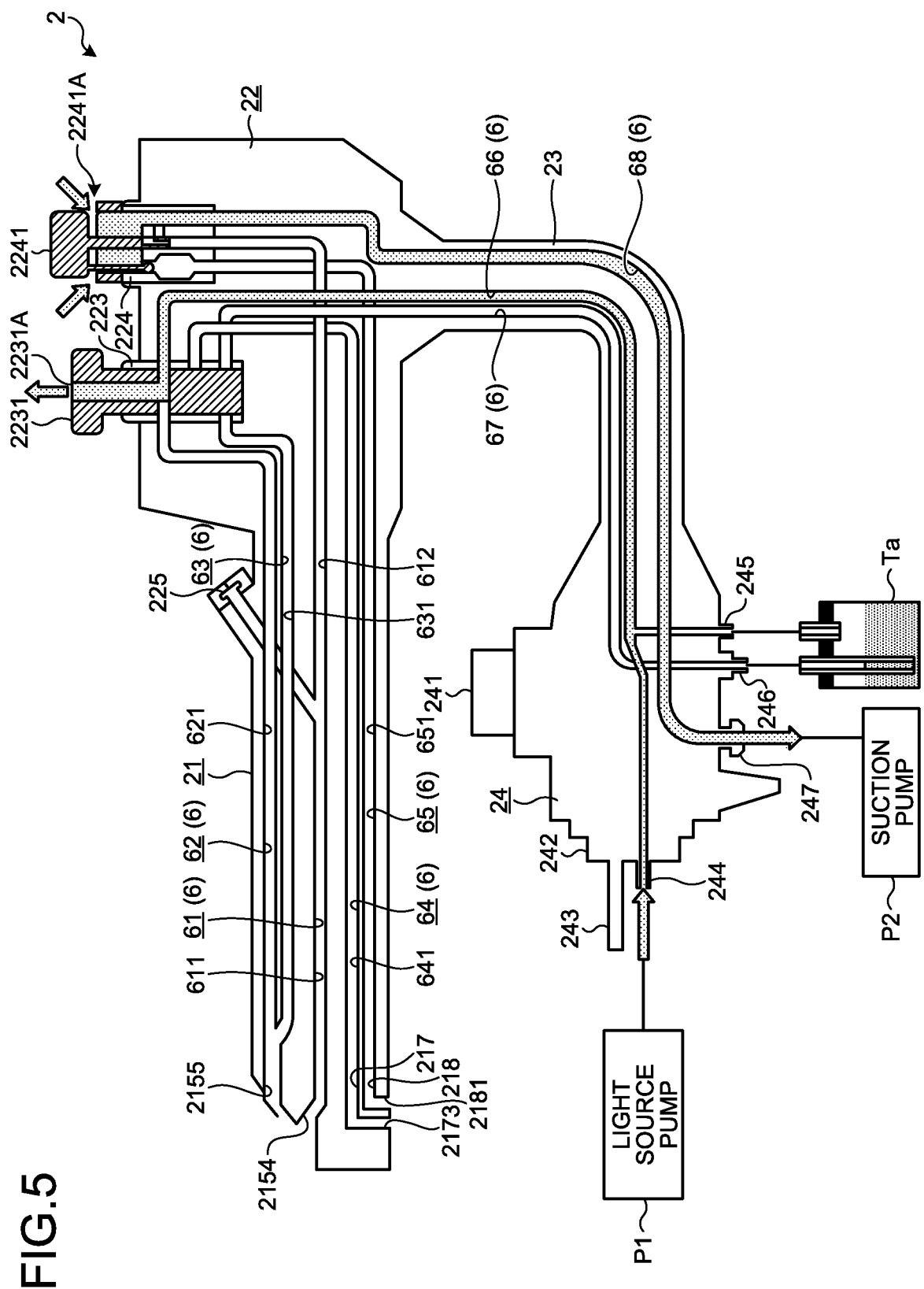
FIG. 5 is a diagram for explaining a connection status of the plurality of pipelines depending on operation of first and second pipeline switching valves.

FIG. 5 is a diagram illustrating a connection status of the plurality of pipelines 6 in the case where no operation is performed on the first and second pipeline switching valves 2231 and 2241 (in the case of no operation).

In the case of no operation on the first pipeline switching valve 2231, the air discharged from the light source pump P1 flows into the first cylinder 223 via the first proximal-end-side pipeline 66 and is also discharged to the outside via a leak hole 2231A formed in the first pipeline switching valve 2231.

Meanwhile, in the case of no operation performed on the second pipeline switching valve 2241, as the suction pump P2 is driven, the air outside the ultrasound endoscope 2 flows into the second cylinder 224 via a leakage clearance 2241A in the second pipeline switching valve 2241 and is sucked by the suction pump P2 via the third proximal-end-side pipeline 68.

That is, in the case of the non-operation, the first to fifth distal-end-side pipelines 61 to 65 and the first to third proximal-end-side pipelines 66 to 68 are not connected, and the distal end of the insertion portion 21 performs neither air supply, water supply, nor suction.

Figure 6:
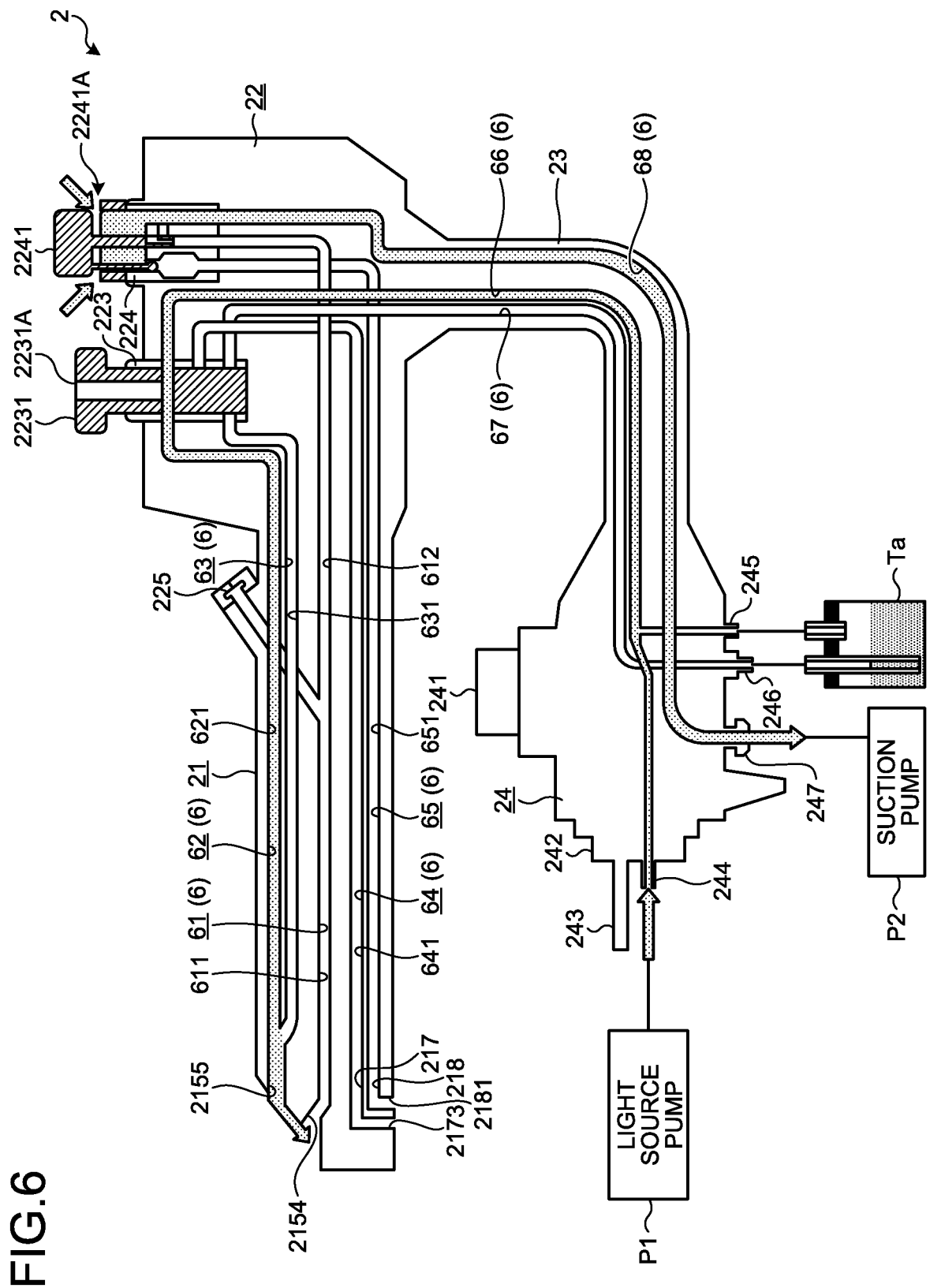
FIG. 6 is a diagram for explaining a connection status of the plurality of pipelines depending on operation of the first and second pipeline switching valves.

FIG. 6 illustrates a connection status of the plurality of pipelines 6 in the case where the leak hole 2231A of the first pipeline switching valve 2231 is closed with a finger. Note that no operation is performed on the second pipeline switching valve 2241 like in FIG. 5.

In the case where the leak hole 2231A is closed with a finger, the second distal-end-side pipeline 62 and the first proximal-end-side pipeline 66 are connected (communicated) via the first pipeline switching valve 2231. The air from the light source pump P1 is discharged, via the first proximal-end-side pipeline 66, the first cylinder 223, the first pipeline switching valve 2231, and the second distal-end-side pipeline 62, toward the imaging hole 2153 (objective optical system (not illustrated)) from the air/water supply hole 2155.

Figure 7:
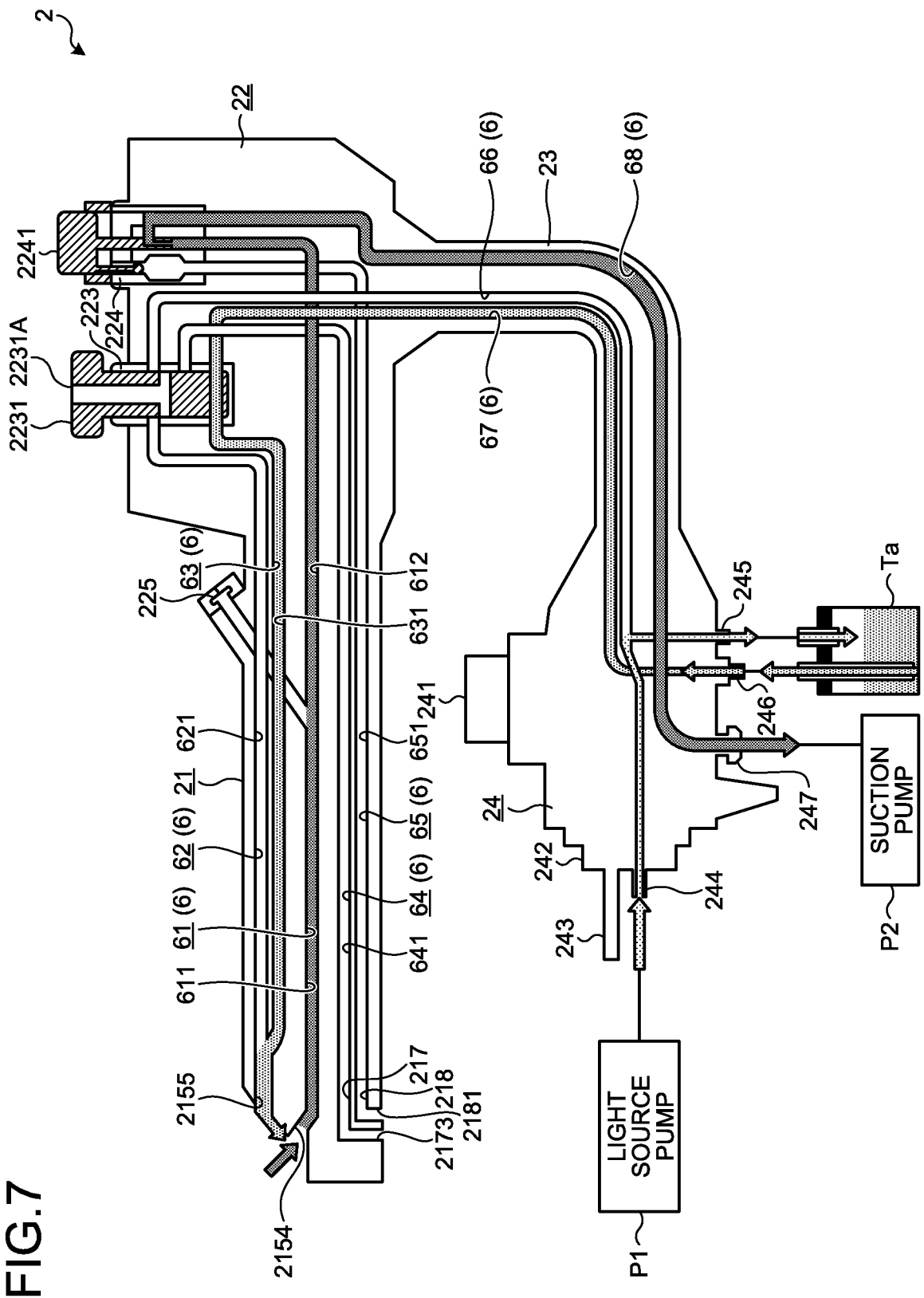
FIG. 7 is a diagram for explaining a connection status of the plurality of pipelines depending on operation of the first and second pipeline switching valves.

FIG. 7 illustrates a connection status of the plurality of pipelines 6 in the case where the first and second pipeline switching valves 2231 and 2241 are pushed by one step.

In the case where the first pipeline switching valve 2231 is pushed by one step, the other end of the first proximal-end-side pipeline 66 is closed by the first pipeline switching valve 2231, and the third distal-end-side pipeline 63 and the second proximal-end-side pipeline 67 are connected (communicated) via the first pipeline switching valve 2231. Then, the air discharged from the light source pump P1 flows into the water supply tank Ta via the first proximal-end-side pipeline 66 to pressurize the inside of the water supply tank Ta, thereby causing water to flow out from the water supply tank Ta. The water from the water supply tank Ta is discharged, via the second proximal-end-side pipeline 67, the first cylinder 223, the first pipeline switching valve 2231, and the third distal-end-side pipeline 63, toward the imaging hole 2153 (objective optical system (not illustrated)) from the air/water supply hole 2155.

Meanwhile in the case where the second pipeline switching valve 2241 is pushed by one step, the first distal-end-side pipeline 61 and the third proximal-end-side pipeline 68 are connected (communicated) via the second pipeline switching valve 2241. Then, liquid inside the subject flows from the treatment instrument channel 2154 into the first distal-end-side pipeline 61 and is sucked by the suction pump P2 via the second cylinder 224, the second pipeline switching valve 2241, and the third proximal-end-side pipeline 68. Note that, in the case where liquid inside the subject is sucked from the treatment instrument channel 2154 in this manner, the treatment instrument inserting port 225 is closed, and a forceps plug (not illustrated) is attached to the treatment instrument inserting port 225 such that the suction pressure is applied to the distal end side (the side of the treatment instrument channel 2154).

Figure 8:
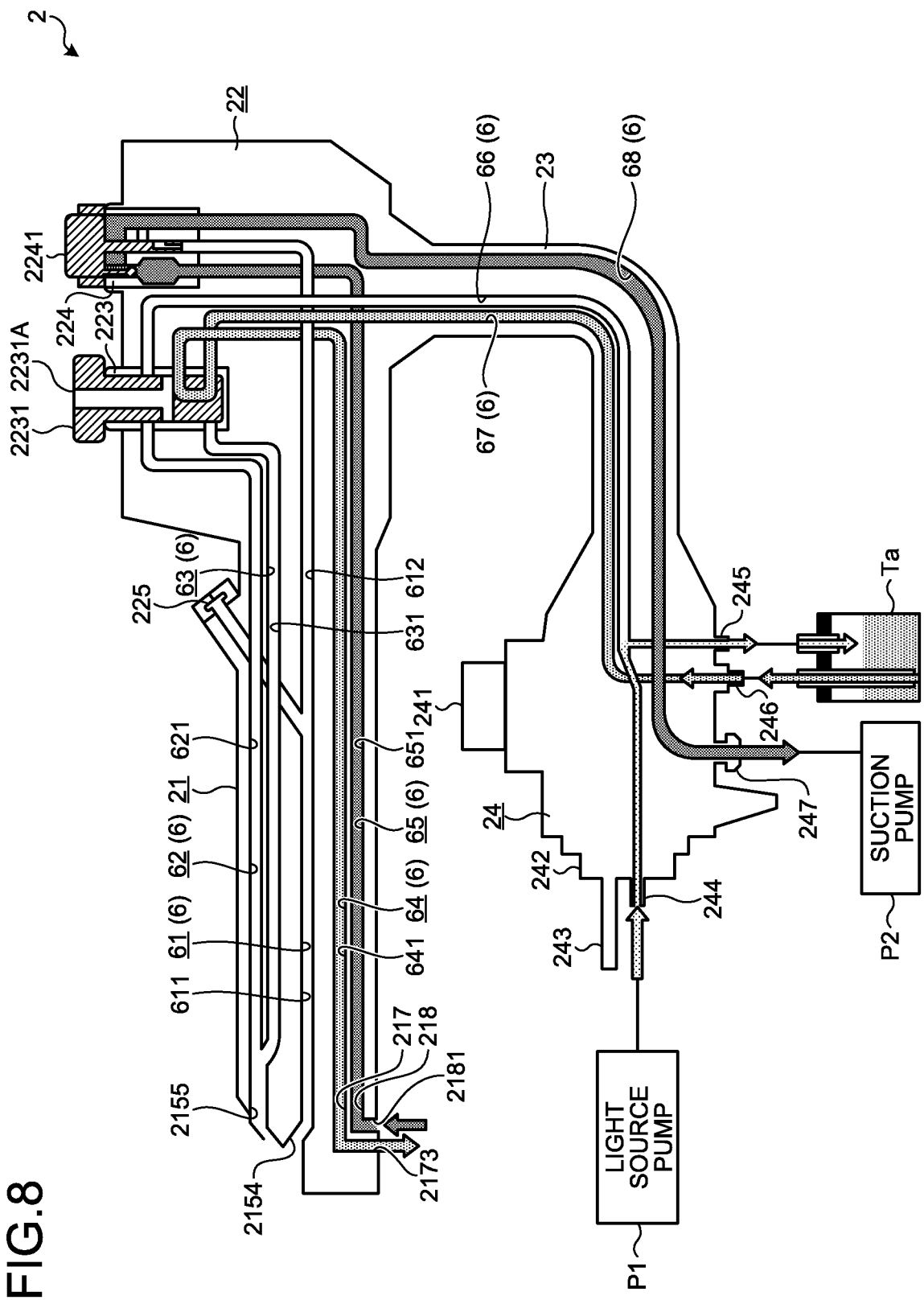
FIG. 8 is a diagram for explaining a connection status of the plurality of pipelines depending on operation of the first and second pipeline switching valves.

FIG. 8 illustrates a connection status of the plurality of pipelines 6 in the case where the first and second pipeline switching valves 2231 and 2241 are pushed by two steps.

In the case where the first pipeline switching valve 2231 is pushed by two steps, the state where the other end of the first proximal-end-side pipeline 66 is closed by the first pipeline switching valve 2231 is maintained, and the fourth distal-end-side pipeline 64 and the second proximal-end-side pipeline 67 are connected (communicated) via the first pipeline switching valve 2231. Then, like in the case where the first pipeline switching valve 2231 is pushed by one step, the air discharged from the light source pump P1 flows into the water supply tank Ta via the first proximal-end-side pipeline 66 to pressurize the inside of the water supply tank Ta, thereby causing water to flow out from the water supply tank Ta. The water from the water supply tank Ta is supplied, via the second proximal-end-side pipeline 67, the first cylinder 223, the first pipeline switching valve 2231, and the fourth distal-end-side pipeline 64, toward the scanning surface SS from the scanning surface supply port 2173.

That is, the fourth distal-end-side pipeline 64 (water supply hole 217) has a function as a supply pipeline according to the disclosure. In addition, the first pipeline switching valve 2231 has a function as a pipeline switching valve according to the disclosure.

Note that, in the case where a balloon (not illustrated) is attached, water supplied from the scanning surface supply port 2173 fills the inside of the balloon.

Meanwhile in the case where the second pipeline switching valve 2241 is pushed by two steps, the fifth distal-end-side pipeline 65 and the third proximal-end-side pipeline 68 are connected (communicated) via the second pipeline switching valve 2241. Then, liquid inside the subject (for example, water inside the balloon) flows from the suction port 2181 into the fifth distal-end-side pipeline 65 and is sucked by the suction pump P2 via the second cylinder 224, the second pipeline switching valve 2241, and the third proximal-end-side pipeline 68.

That is, the fifth distal-end-side pipeline 65 (suction hole 218) has a function as a suction pipeline according to the disclosure.

The ultrasound endoscope 2 according to the present embodiment described above has the following effects.

Figure 9:
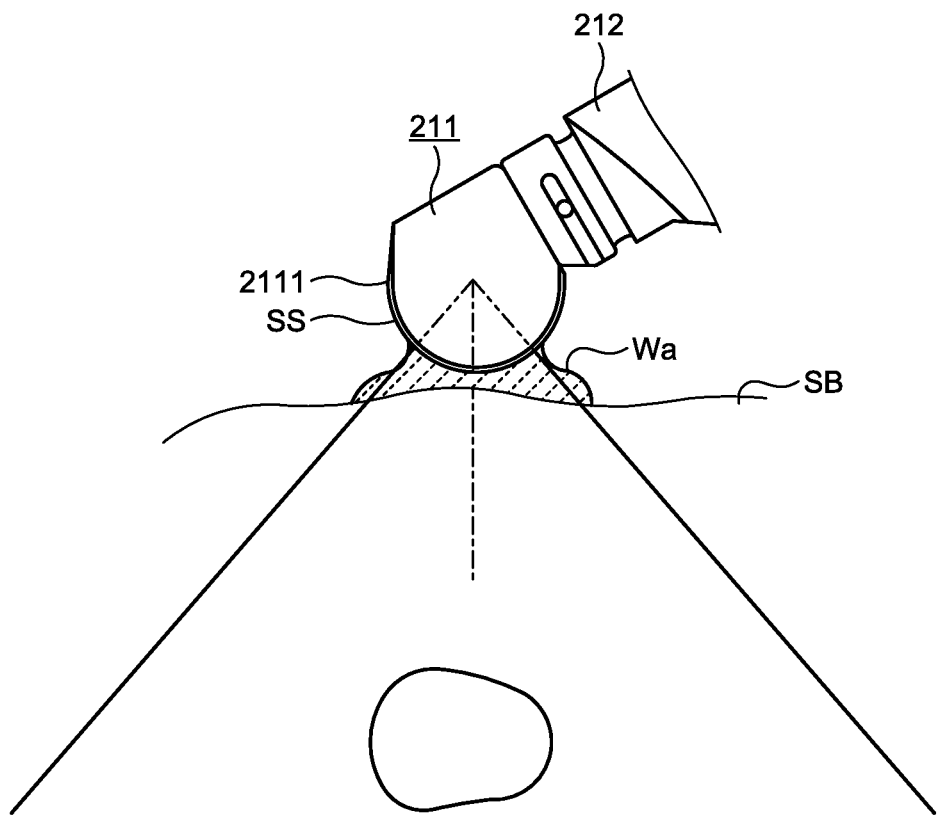
FIG. 9 is a diagram for explaining the effect of the embodiment of the disclosure.

FIG. 9 is a diagram for explaining the effect of the embodiment of the disclosure.

In the ultrasound endoscope 2 according to the present embodiment, the rigid member 212 includes the water supply hole 217 having the scanning surface supply port 2173 for supplying water toward the scanning surface SS. Moreover, when the distal end of the insertion portion 21 is viewed from the upper side thereof, the water supply hole 217 is formed such that a part of the supply central axis Ax1 is positioned within the scanning surface SS. Furthermore, when the distal end of the insertion portion 21 is viewed from above, the water supply hole 217 is formed such that the supply central axis Ax1 intersects with the scanning central axis Ax1 at an acute angle.

Forming the water supply hole 217 in the above manner results in, when water is supplied to the scanning surface SS from the scanning surface supply port 2173, capillary phenomenon by a gap between a body wall SB and the scanning surface SS and the surface tension of the water as illustrated in FIG. 9, thus resulting in a liquid layer Wa formed between the body wall SB and the scanning surface SS. Therefore, the liquid layer Wa prevents the propagation rate of ultrasound waves from being degraded, thus enabling to obtain an ultrasound image of a range necessary for ultrasound diagnosis or FNA techniques.

Therefore, according to the ultrasound endoscope 2 according to the present embodiment, there is an effect that an appropriate ultrasound image can be obtained without using the degassed water-filling method or the balloon method.

In particular, the scanning surface supply port 2173 is provided at a position closer to the distal end side than the balloon attachment groove 2161. Therefore, the scanning surface supply port 2173 can be formed at a position closer to the scanning surface SS, and the liquid layer Wa can be preferably formed between the body wall SB and the scanning surface SS.

In addition, only the scanning surface supply port 2173 is provided as a supply port for supplying the ultrasound wave transfer medium at a position closer to the distal end side than the balloon attachment groove 2161. That is, the water supply hole 217 is a pipeline for supplying water toward the scanning surface SS, and in the case of using a balloon (not illustrated), a pipeline for filling the balloon with water. Since the two pipelines are shared in this manner, the diameter of the insertion portion 21 (rigid member 212) can be reduced as compared with the case where the two pipelines are included separately.

Furthermore, when the first pipeline switching valve 2231 is pushed by two steps, water is supplied to the scanning surface SS via the scanning surface supply port 2173. Therefore, the liquid layer Wa can be formed between the body wall SB and the scanning surface SS by simple operation, thereby enhancing convenience.

Other Embodiments

Although the embodiment for carrying out the disclosure has been described above, the disclosure is not limited only to the embodiment described above.

In the embodiment described above, water is employed as the ultrasound wave transfer medium supplied toward the scanning surface SS; however, the disclosure is not limited thereto, and other fluids such as liquid paraffin or an aqueous solution of carboxymethyl cellulose may be used.

In the embodiment described above, when the distal end of the insertion portion 21 is viewed from the upper side thereof, the water supply hole 217 is formed such that the supply central axis Ax1 intersects with the insertion direction ID of the insertion portion 21 at an acute angle; however, the disclosure is not limited thereto. As long as a part of the supply central axis Ax1 is positioned within the scanning surface SS when the distal end of the insertion portion 21 is viewed from the upper side thereof, the water supply hole 217 may be formed such that the supply central axis Ax1 is parallel to the insertion direction ID.

Furthermore in the embodiment described above, when the distal end of the insertion portion 21 is viewed from the side, the water supply hole 217 is formed such that the supply central axis Ax1 intersects with the scanning central axis Ax1 at an acute angle; however, the disclosure is not limited thereto. As long as a part of the supply central axis Ax1 is positioned within the scanning surface SS when the distal end of the insertion portion 21 is viewed from the upper side thereof, the water supply hole 217 may be formed such that the supply central axis Ax1 is parallel to the scanning central axis Ax2, or the water supply hole 217 may be formed such that the supply central axis Ax1 does not intersect with the scanning central axis Ax2.

In the embodiment described above, the transducer 2111 is a convex type; however, the disclosure is not limited thereto, and a transducer which is a radial type may be adopted. Even in the case of where a transducer of a radial type is adopted, it is preferable that the water supply hole (supply pipeline) is formed such that a part of the supply central axis is positioned within the scanning surface when viewed from a direction orthogonal to the insertion direction into the subject and the scanning surface of the transducer.

In the above-described embodiment, the endoscope system 1 has both the function of generating an ultrasound image and the function of generating an endoscopic image; however, the disclosure is not limited to this and may be configured to have only the function of generating an ultrasound image.

In the above-described embodiments, the endoscope system 1 may observe the inside of a subject such as a machine structure in the industrial field without being limited to the medical field.

According to an ultrasound endoscope of the disclosure, there is an effect that an appropriate ultrasound image can be obtained without using the degassed water-filling method or the balloon method.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound endoscope provided with an insertion portion to be inserted into a subject along a first direction which is an insertion direction, the ultrasound endoscope comprising:
    a transducer having a scanning surface that scans with an ultrasound wave along a second direction;
    a supply pipeline configured to supply an ultrasound wave transfer medium; and
    a rigid member connected to a proximal end side of the transducer, the rigid member formed with a scanning surface supply port configured to supply the ultrasound wave transfer medium supplied from the supply pipeline in a direction intersecting with the first direction and the second direction.

2. The ultrasound endoscope according to claim 1, wherein the transducer is a convex type having a scanning surface having a convex shape.

3. The ultrasound endoscope according to claim 1, wherein the rigid member is formed with a balloon attachment groove for attachment of a balloon to be filled with the ultrasound wave transfer medium, and the scanning surface supply port is provided at a position closer to a distal end of the rigid member than the balloon attachment groove.

4. The ultrasound endoscope according to claim 3, wherein in a state in which the balloon is attached, the ultrasound wave transfer medium flowing out from the scanning surface supply port fills an inside of the balloon.

5. The ultrasound endoscope according to claim 3, wherein in a state in which the balloon is not attached, the ultrasound wave transfer medium flowing out from the scanning surface supply port is supplied over the scanning surface of the transducer.

6. The ultrasound endoscope according to claim 3, wherein the rigid member further comprises a suction port configured to suck the ultrasound wave transfer medium, the suction port being provided at a position closer to the distal end than the balloon attachment groove.

7. The ultrasound endoscope according to claim 1, further comprising a pipeline switching valve configured to switch a connection status of a plurality of pipelines including the supply pipeline depending on pushing operation, wherein operation of the switching valve causes the ultrasound wave transfer medium to be supplied from the scanning surface supply port via the supply pipeline.

\* \* \* \* \*